(12) United States Patent
Cai et al.

(10) Patent No.: US 11,815,497 B2
(45) Date of Patent: Nov. 14, 2023

(54) TRIAXIAL TEST APPARATUS FOR MEASURING ERODED SOIL PARTICLE UNDER ACTION OF SEEPAGE FORCE

(71) Applicant: ZHEJIANG UNIVERSITY OF TECHNOLOGY, Hangzhou (CN)

(72) Inventors: Yuanqiang Cai, Hangzhou (CN); Honglei Sun, Hangzhou (CN); Tingyu Wu, Hangzhou (CN); Yaochen Jiang, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 31 days.

(21) Appl. No.: 17/584,393

(22) Filed: Jan. 26, 2022

(65) Prior Publication Data
US 2022/0236156 A1 Jul. 28, 2022

(30) Foreign Application Priority Data
Jan. 28, 2021 (CN) .......................... 202110114668.9

(51) Int. Cl.
| | |
|---|---|
| *G01N 3/12* | (2006.01) |
| *G01N 15/08* | (2006.01) |
| *G01N 15/02* | (2006.01) |
| *G01N 3/02* | (2006.01) |
| *G01N 33/24* | (2006.01) |

(52) U.S. Cl.
CPC ................. *G01N 3/12* (2013.01); *G01N 3/02* (2013.01); *G01N 33/24* (2013.01); *G01N 2203/0019* (2013.01); *G01N 2203/0256* (2013.01)

(58) Field of Classification Search
CPC .... G01N 15/088; G01N 29/024; G01N 33/18; G01N 29/14; G01N 3/10; G01N 1/34; G01N 1/286; G01N 1/36; G01N 3/12; G01N 3/24; G01N 5/04; G01N 13/04; G01N 33/24; G01N 15/0826; G01N 3/02; G01N 3/567; G01N 3/08; G01N 3/565; G01N 17/00; G01N 2203/0019; G01N 2203/0256; G01D 21/02
See application file for complete search history.

(56) References Cited

FOREIGN PATENT DOCUMENTS

| CN | 208334084 U | * | 1/2019 |
|---|---|---|---|
| CN | 110940610 A | * | 3/2020 |

* cited by examiner

*Primary Examiner* — Brandi N Hopkins (57) ABSTRACT

A triaxial test apparatus for measuring eroded soil particles under action of seepage force includes a constant-flow seepage system, a soil particle transport grading measurement system, a large-range volume pressure control vacuum system and a data processing and analyzing system, where the constant-flow seepage system is connected to the soil particle transport grading measurement system and the large-range volume pressure control vacuum system by means of pipelines separately, the data processing and analyzing system includes a data acquisition device and a computer, the constant-flow seepage system, the soil particle transport grading measurement system and the large-range volume pressure control vacuum system are connected to the data acquisition device by means of lines separately, and the computer is connected to the data acquisition device by means of a line.

9 Claims, 5 Drawing Sheets

TRIAXIAL TEST APPARATUS FOR MEASURING ERODED SOIL PARTICLE UNDER ACTION OF SEEPAGE FORCE

TECHNICAL FIELD

The present invention relates to the technical field of geotechnical engineering, in particular to a triaxial test apparatus for measuring eroded soil particles under action of seepage force.

BACKGROUND ART

The seepage deformation of the soil can be divided into soil flowing, piping (also commonly referred to as internal erosion), contact scouring, and contact run-off. Soil flowing refers to the phenomenon that under action of seepage force, when the effective stress between particles is zero, particle groups suspend and move, which is called as soil flowing or sand flowing, most of the phenomenon occurs in saturated fine sand, silty sand and silt with uniform particle granular composition, it generally occurs suddenly and greatly harms engineering, soil flowing is formed by soil particles with various particle sizes moving, and does not refer to that the fine soil particles pass through the pores of the coarse soil particles to run off; and piping refers to the phenomenon that the fine particles are washed away or brought out of the pores of the coarse particles under the action of seepage.

A saturation mode of an existing device for measuring soil sample seepage erosion is that a soil sample is immersed in water for saturation, an erosion water head is provided by a suspension water tank, a seepage erosion path is from top to bottom, and lost particles after soil body erosion and the water are simply collected together. The seepage-erosion test method has the defects: 1, the sample is placed under the water head provided by the hoisted water tank for seepage erosion test, the provided water head range is limited, and the simulation erosion under the condition of coupling water head cyclic change and complex stress cyclic change cannot be achieved; 2, the lost particles after the soil body is eroded are not collected in a graded manner; and 3, the soil sample can only be immersed in water for rough saturation, and the soil body cannot meet the requirement for high saturation of the saturated soil sample in a unit body test, so the influence of saturation on the mechanical property of the sample cannot be avoided.

SUMMARY

The technical problem to be solved by the present invention is to provide a triaxial test apparatus for measuring eroded soil particles under action of seepage force. The test apparatus may simulate current crustal stress, so as to simulated and dynamically observe erosion phenomenon of a soil sample under the action of specific seepage force.

To this end, a triaxial test apparatus for measuring eroded soil particles under action of seepage force provided in the present invention includes a constant-flow seepage system, a soil particle transport grading measurement system, a large-range volume pressure control vacuum system and a data processing and analyzing system, where the constant-flow seepage system is connected to the soil particle transport grading measurement system and the large-range volume pressure control vacuum system by means of pipelines separately, the data processing and analyzing system includes a data acquisition device and a computer, the constant-flow seepage system, the soil particle transport grading measurement system and the large-range volume pressure control vacuum system are connected to the data acquisition device by means of lines separately, and the computer is connected to the data acquisition device by means of a line.

Preferably, the constant-flow seepage system includes a triaxial cell, an axial-force applying unit and a confining pressure applying unit, the triaxial cell including a cell outer cover, a base and a top cap, where a soil sample is arranged between the base and the top cap, and the cell outer cover is mounted on the base; the axial applying unit includes a first servo machine box and an upper cover, the base is mounted on the first servo machine box, the first servo machine box is connected to an axial piston rod, an upper portion of the axial piston rod is connected to the base, the upper cover is arranged on the top cap, and the upper cover is provided with an axial displacement sensor and an axial pressure sensor; and the confining pressure applying unit includes a second servo machine box, an oil tank and a confining pressure device, the confining pressure device being connected to the base by means of a pipeline, and the oil tank being mounted on the second servo machine box and connected to the base by means of a fifth pipeline.

Preferably, a taper hole is provided in the base, a first open hole and a second open hole are provided in the taper hole, the first open hole is connected to the large-range volume pressure control vacuum system by means of a first pipeline, a first flowmeter is arranged on the pipeline, the second open hole is connected to a confining pressure device by means of a second pipeline, the top cap is provided with an inverted taper hole, a third open hole and a fourth open hole are provided in the inverted taper hole, the third open hole is connected to a pressure sensor by means of a third pipeline, the fourth open hole is connected to the soil particle transport grading measurement system by means of a fourth pipeline, and a sensor and a second flowmeter are arranged on the fourth pipeline.

Preferably, the soil particle transport grading measurement system includes a first water storage tank and a multi-stage filter tank, the multi-stage filter tank being arranged in the first water storage tank, a water inlet is provided in the first water storage tank, an end, located in an inner cavity of the first water storage tank, of the water inlet is connected to a bell-mouthed pipeline, the other end of the bell-mouthed pipeline is in butt joint with the multi-stage filter tank, an end, located outside the first water storage tank, of the water inlet is provided with a first volume pressure controller, the first volume pressure controller is connected to the constant-flow seepage system by means of the fourth pipeline, and a water storage device is connected to a bottom of the first water storage tank by means of a sixth pipeline.

Preferably, one side of the first water storage tank is connected to a first air pump by means of a seventh pipeline, a two-way valve is arranged at a joint of the first water storage tank and the pipeline, a third flowmeter is arranged on the sixth pipeline, and a turbidimeter is arranged on the water storage device.

Preferably, the large-range volume pressure control vacuum system includes a second water storage tank and a second air pump, a blade fan is mounted in the second water storage tank, a two-way valve is arranged at an opening in one side of the second water storage tank, the second air pump is connected to the two-way valve by means of an eighth pipeline, an external second volume pressure controller is connected to a bottom of the second water storage tank by means of a pipeline, and the second volume pressure controller is connected to the constant-flow seepage system by means of the first pipeline.

Preferably, the first volume pressure controller, the second volume pressure controller, the first flowmeter, the second flowmeter, the third flowmeter, the confining pressure device, the pressure sensor, the sensor, the axial displacement sensor and the axial pressure sensor are connected to the data acquisition device by means of lines separately.

Preferably, an upper end and a lower end of the soil sample are provided with a porous bottom plate and water-permeable paper respectively.

Preferably, the multi-stage filter tank consists of at least three steel wire mesh layers, and the steel wire mesh layers have different pore diameters.

Preferably, the taper hole and the inverted taper hole are funnel-shaped.

The present disclosure has the following beneficial effects:

1. By arranging a constant-flow seepage system, a soil particle transport grading measurement system, a large-range volume pressure control vacuum system, and a data processing and analyzing system, an erosion phenomenon of a soil sample under the action of specific seepage force is simulated and dynamically observed, so as to provide an accurate and effective basic test data for research of a geological disaster causing mechanism corresponding to the erosion phenomenon.

2. The test apparatus applies seepage force under a back pressure saturation condition based on a triaxial test system and measures a seepage-erosion phenomenon, is suitable for various triaxial instruments, has high compatibility, and may meet different experimental requirements.

3. By setting confining pressure and back pressure, the confining pressure and the back pressure are supplied to the soil sample so as to simulate the current crustal stress, by setting the constant-flow seepage system, stable upward seepage is provided for the soil sample, back pressure saturation may be carried out on the soil sample before a test, and the back pressure is maintained in a whole experiment process.

4. A porous bottom plate is arranged on a base of a triaxial cell and an upper portion of the soil sample, a soil particle outflow channel is provided in a top cap, and a grading collection device is arranged, such that eroded soil particles may flow into the soil particle transport grading measurement system by means of the soil particle outflow channel of the top cap to be graded and collected, so as to provided basic experimental data for particle component change after the soil sample is corroded.

5. A turbidimeter is arranged in a water storage device of the soil particle transport grading measurement system so as to detect whether soil particles flowing out during seepage erosion are completely filtered.

DETAILED DESCRIPTION OF THE EMBODIMENTS

The present invention will be further elaborated hereafter in conjunction with accompanying drawings and the embodiments. The same parts are denoted by the same reference numerals. It should be noted that, as used in the following description, the words "front", "rear", "left", "right", "upper" and "lower" refer to directions in the accompanying drawings, and the words "bottom" and "top", "inner" and "outer" refer to directions toward or away from, respectively, a geometric center of a particular component.

Figure 1:
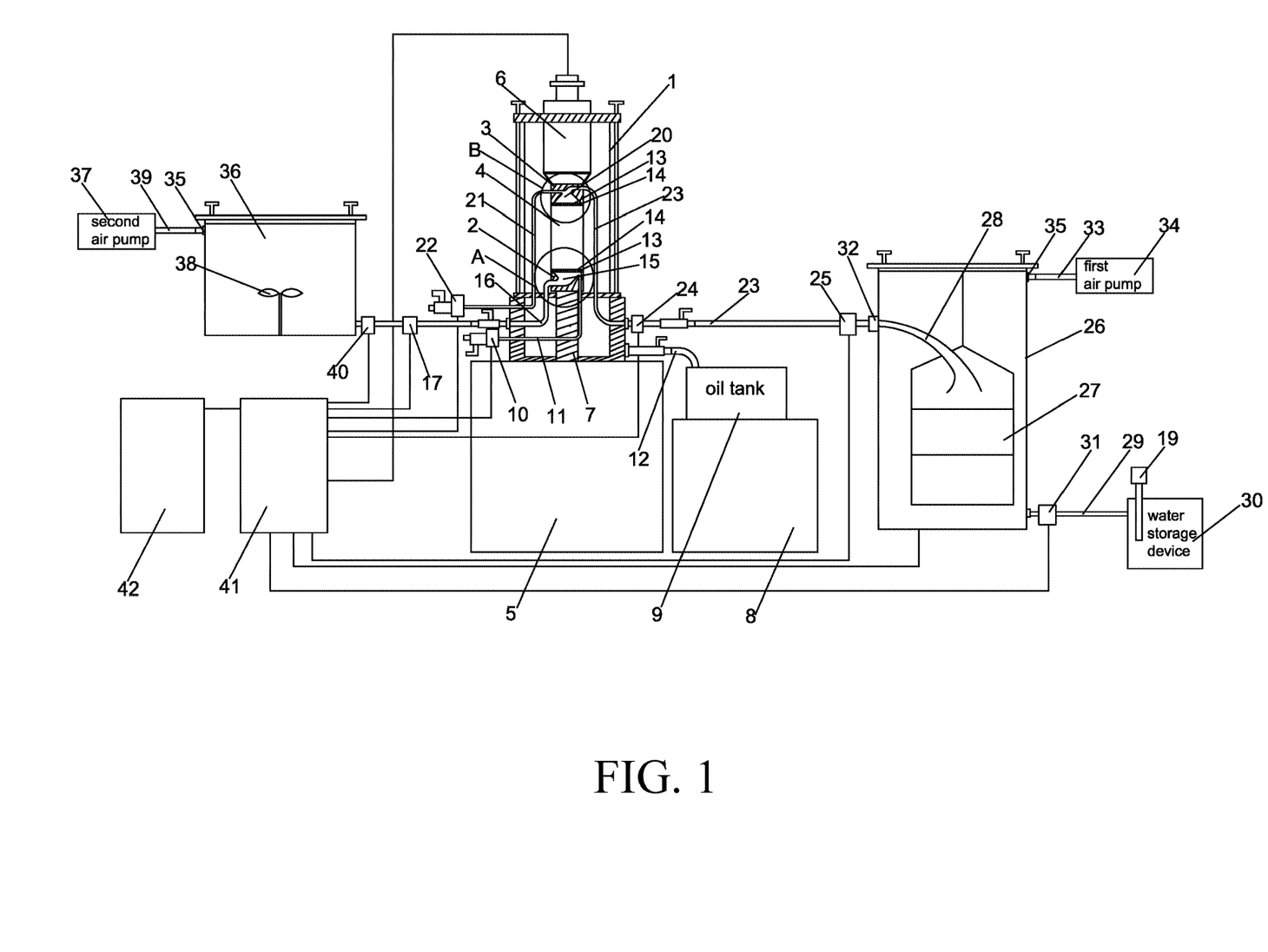
FIG. 1 is a structural schematic diagram of a triaxial test apparatus for measuring eroded soil particles under action of seepage force provided in the present invention.

With reference to FIG. 1, the present invention provides a triaxial test apparatus for measuring eroded soil particles under action of seepage force. The triaxial test apparatus includes a constant-flow seepage system A, a soil particle transport grading measurement system B, a large-range volume pressure control vacuum system C and a data processing and analyzing system D. The constant-flow seepage system A is connected to the soil particle transport grading measurement system B and the large-range volume pressure control vacuum system C by means of pipelines separately, the data processing and analyzing system D includes a data acquisition device 41 and a computer 42, the constant-flow seepage system, the soil particle transport grading measurement system and the large-range volume pressure control vacuum system are connected to the data acquisition device by means of lines separately, and the computer is connected to the data acquisition device by means of a line.

Figure 2:
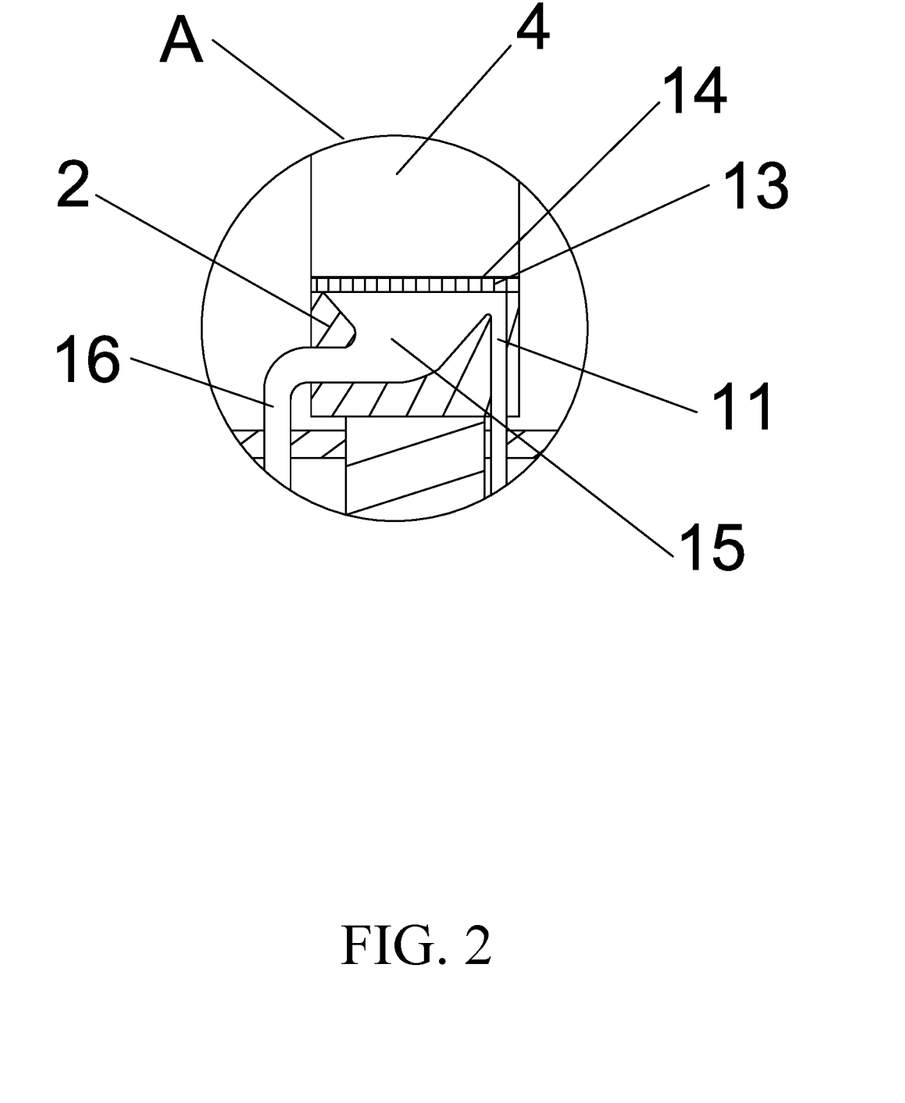
FIG. 2 is a structural schematic diagram of position A of the triaxial test apparatus for measuring eroded soil particles under action of seepage force in FIG. 1.

The constant-flow seepage system A includes a triaxial cell, an axial-force applying unit and a confining pressure applying unit, the triaxial cell including a cell outer cover 1, a base 2 and a top cap 3, where a soil sample 4 is arranged between the base 2 and the top cap 3, and the cell outer cover 1 is mounted on the base 2. The axial applying unit includes a first servo machine box 5 and an upper cover 6, the base 2 is mounted on the first servo machine box 5, the first servo machine box 5 is connected to an axial piston rod 7, an upper portion of the axial piston rod 7 is connected to the base 2. The upper cover 6 is arranged on the top cap 3, the upper cover 6 is provided with an axial displacement sensor and an axial pressure sensor, and axial pressure is provided for the soil sample by means of the axial piston rod 7. The confining pressure applying unit includes a second servo machine box 8, an oil tank 9 and a confining pressure device 10, the confining pressure device 10 being connected to the base 2 by means of a second pipeline 11, and the confining pressure device 10 being a confining pressure sensor. The oil tank 9 is mounted on the second servo machine box 8, the oil tank 9 is connected to the base by means of a fifth pipeline 12, and the base is in communication with an inner cavity of the cell. Oil is injected into the triaxial cell by means of the oil tank 9, the second servo machine box 8 and the fifth pipeline 12, a cavity of the triaxial cell is filled with the oil, the oil is wrapped around a periphery of the soil sample, shaft closing is conducted in an oil filling process, confining pressure is set by means of the confining pressure sensor after oil filling, and the confining pressure is provided for the soil sample 4.

Figure 3:
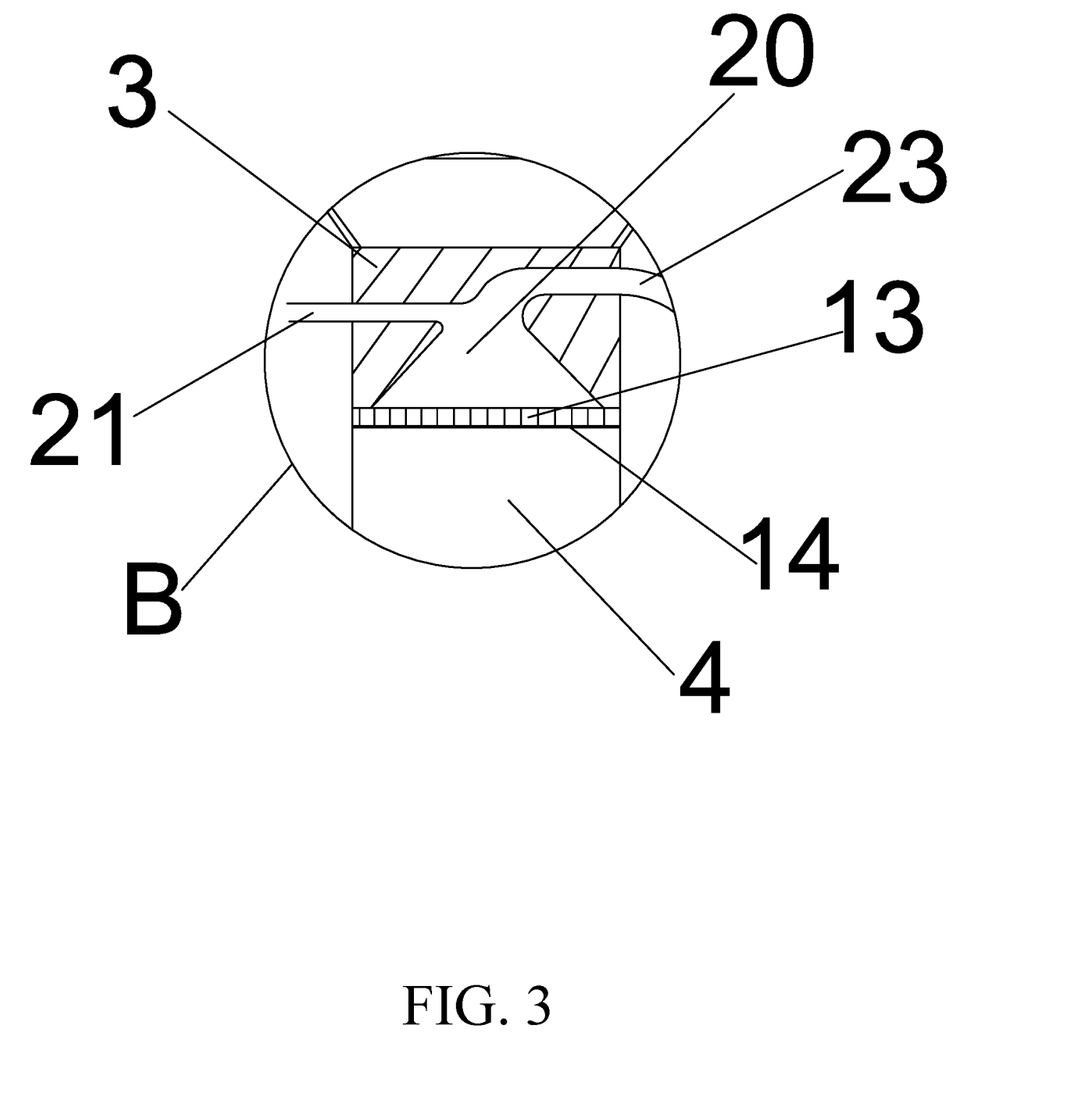
FIG. 3 is a structural schematic diagram of position B of the triaxial test apparatus for measuring eroded soil particles under action of seepage force in FIG. 1.

An upper end and a lower end of the soil sample 4 are provided with a porous bottom plate 13 and water-permeable paper 14 respectively, that is, the porous bottom plate 13 and the water-permeable paper 14 are arranged between the soil sample and the base, and the porous bottom plate 13 and the water-permeable paper 14 are also arranged between the soil sample and the top cap. A taper hole 15 is provided in the base, the taper hole 15 is funnel-shaped, a first open hole and a second open hole are provided in the taper hole. The first open hole is connected to the external large-range volume pressure control vacuum system C by means of a first pipeline 16, a first flowmeter 17 is arranged on the first pipeline 16, and the constant-flow seepage system A is connected to the large-range volume pressure control vacuum system C by means of the first pipeline 16. The second open hole is connected to the confining pressure device 10 by means of a second pipeline 11. During testing, the large-range volume pressure control vacuum system provides inlet water for the constant-flow seepage system A by means of the first pipeline 16, the water is input into the base 2 by means of the first pipeline and permeates into the soil sample by means of the first open hole and the porous bottom plate 13 and the water-permeable paper 14 at the lower end of the soil sample, and stable upward seepage and erosion are provided for the soil sample. The top cap is provided with an inverted taper hole 20, the inverted taper hole 20 is funnel-shaped, a third open hole and a fourth open hole are provided in the inverted taper hole, and the inverted taper hole 20 is provided with an outflow channel for the soil particle. The third open hole is connected to a pressure sensor 22 by means of a third pipeline 21, the fourth open hole is connected to the soil particle transport grading measurement system B by means of a fourth pipeline 23, and a sensor 24 and a second flowmeter 25 are arranged on the fourth pipeline 23. One end of the fourth pipeline 23 is connected to the fourth open hole, and the other end of the fourth pipeline 23 penetrates out of the triaxial cell to be connected to the soil particle transport grading measurement system B. The soil sample seeps upwards, and eroded soil particles passes through the porous bottom plate 13 and the water-permeable paper 14 at an upper end of the soil sample, and then are conveyed to a soil particle transport grading measurement system B by means of the inverted taper hole 20 and the fourth pipeline 23.

Figure 5:
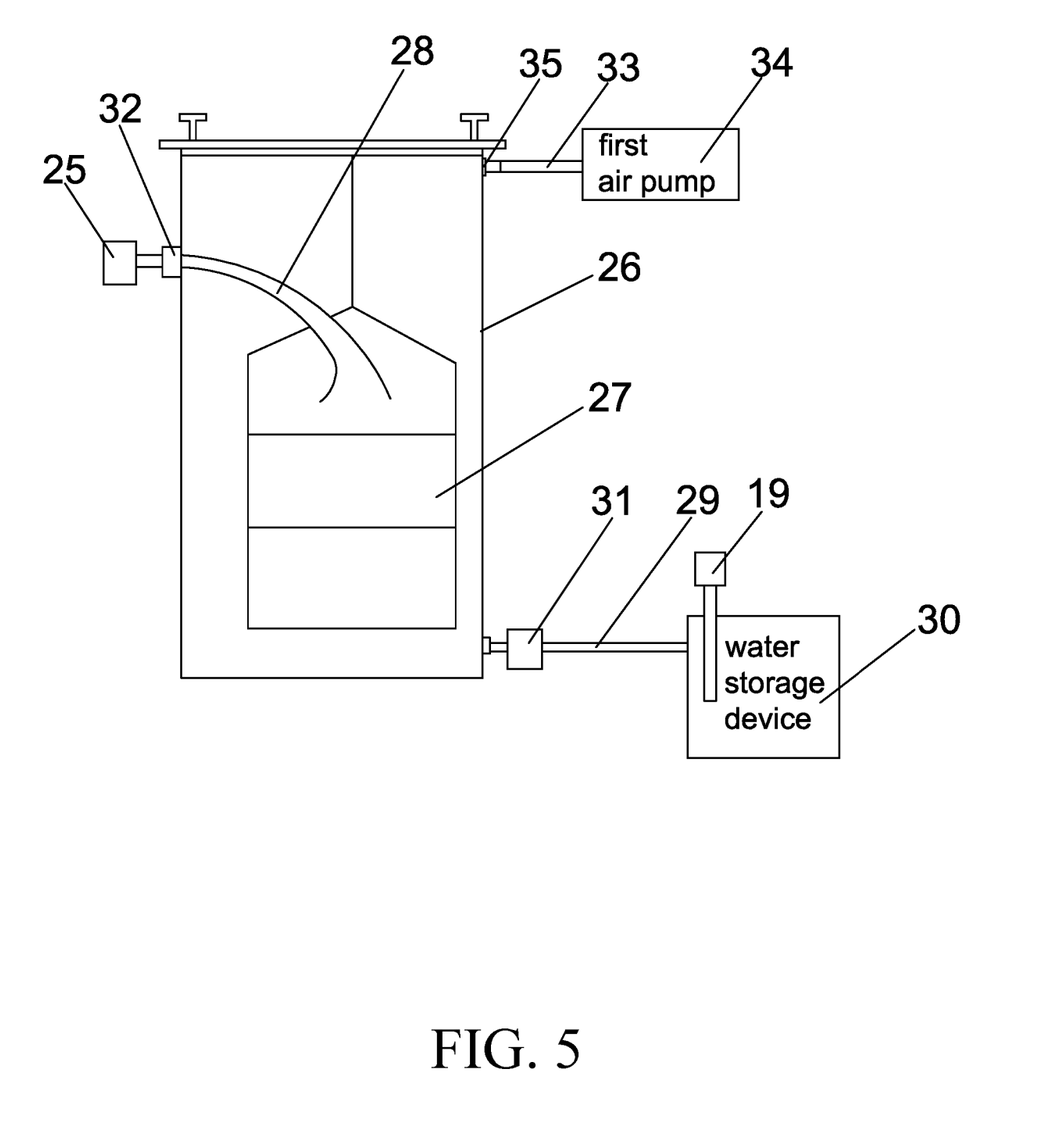
FIG. 5 is a structural schematic diagram of a soil particle transport grading measurement system B of the triaxial test apparatus for measuring eroded soil particles under action of seepage force in FIG. 1.

The soil particle transport grading measurement system B includes a first water storage tank 26 and a multi-stage filter tank 27, the multi-stage filter tank 27 being arranged in the first water storage tank 26, and the multi-stage filter tank 27 is hoisted on a cover plate of the first water storage tank 26. The multi-stage filter tank 27 consists of at least three steel wire mesh layers, the steel wire mesh layers having different pore diameters, and preferably, three steel wire mesh layers are steel wire meshes with three different types of pore diameters. A water inlet is provided in the first water storage tank 26, an end, located in an inner cavity of the first water storage tank 26, of the water inlet is connected to a bell-mouthed pipeline 28, the other end of the bell-mouthed pipeline 28 is in butt joint with the multi-stage filter tank 27. A water storage device 30 is connected to a bottom of the first water storage tank 26 by means of a sixth pipeline 29, and a third flowmeter 31 is arranged on the sixth pipeline 29. The eroded soil particle enters the multi-stage filter tank 27 in the first water storage tank by means of the fourth pipeline 23 and the bell-mouthed pipeline 28. The eroded soil particle is filtered by the multi-stage filter tank, and the filtered water flows into the water storage device 30 by means of a sixth pipeline 29. A turbidimeter 19 is arranged on the water storage device 30, and the turbidimeter 19 is configured to detect whether the soil particles flowing out during seepage erosion are completely filtered.

An end, located outside the first water storage tank, of the water inlet of the first water storage tank 26 is provided with a first volume pressure controller 32, and the other end of the fourth pipeline is connected to the first volume pressure controller 32. One side of the first water storage tank is connected to a first air pump 34 by means of a seventh pipeline 33, and a two-way valve 35 is arranged at a joint of the first water storage tank and the seventh pipeline 33. The first air pump 34 is vacuumized by means of the two-way valve, the water in the first water storage tank 26 is made into air-free water, and back pressure is set for the soil sample by means of the first volume pressure controller 32.

Figure 4:
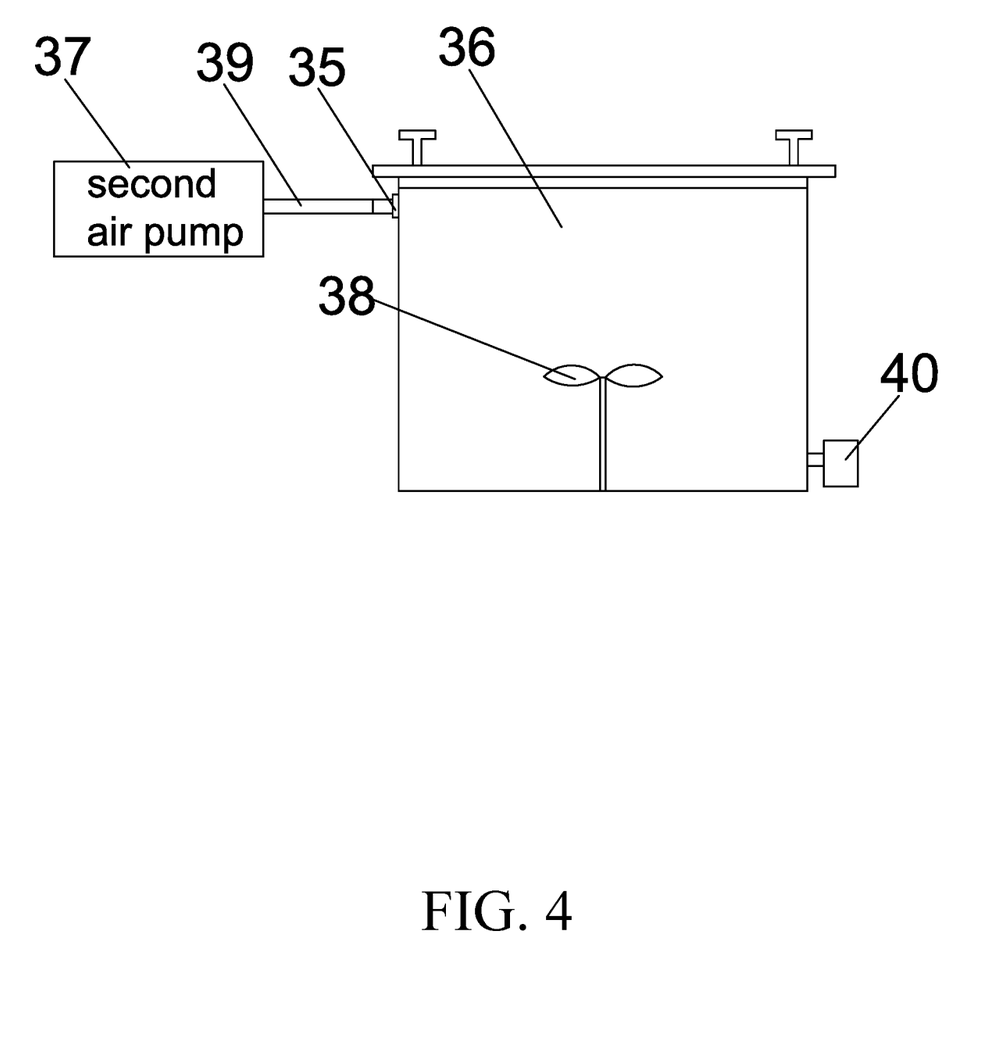
FIG. 4 is a structural schematic diagram of a large-range volume pressure control vacuum system C of the triaxial test apparatus for measuring eroded soil particles under action of seepage force in FIG. 1.

The large-range volume pressure control vacuum system C includes a second water storage tank 36 and a second air pump 37, a blade fan 38 is mounted in the second water storage tank 36, a two-way valve 35 is arranged at an opening in one side of the second water storage tank 36, the second air pump 37 is connected to the two-way valve 35 by means of an eighth pipeline 39, an external second volume pressure controller 40 is connected to a bottom of the second water storage tank 36 by means of the first pipeline 16, and the second volume pressure controller 40 is connected to the constant-flow seepage system A by means of the first pipeline 16. The second air pump 37 is vacuumized by means of the two-way valve 35, meanwhile, the blade fan 38 works, the water in the second water storage tank 36 is made into air-free water, and back pressure is set for the soil sample by means of the second volume pressure controller 40. The first volume pressure controller 32 and the second volume pressure controller 40 apply back pressure to the soil sample.

The first volume pressure controller 32, the second volume pressure controller 40, the first flowmeter 17, the second flowmeter 25, the third flowmeter 31, the confining pressure sensor 10, the pressure sensor 22, the sensor 24, the axial displacement sensor and the axial pressure sensor are connected to the data acquisition device 41 by means of lines separately, and the data acquisition device 41 is connected to the computer 42 by means of a line. The computer sets the back pressure by means of the first volume pressure controller 32 and the second volume pressure controller 40. Flow of the inlet water is controlled and measured by means of the first flowmeter 17, flow of the eroded soil particles is controlled and measured by means of the second flowmeter 25, and flow of outlet water is controlled and measured by means of the third flowmeter 31. The computer 42 sets confining pressure after oil filling by means of the confining pressure sensor 10. A constant-flow seepage system, a soil particle transport grading measurement system, a large-range volume pressure control vacuum system, and a data processing and analyzing system are arranged by means of a computer, an erosion phenomenon of a soil sample under the action of specific seepage force is simulated and dynamically observed, so as to provide an accurate and effective basic test data for research of a geological disaster causing mechanism corresponding to the erosion phenomenon.

Before the test, the first volume pressure controller 32 and the second volume pressure controller 40 are configured to apply the back pressure to the soil sample 4, back pressure saturation is carried out on the soil sample 4, and the back pressure is maintained in the whole experiment process. Oil is injected into the triaxial cell by means of the oil tank 9, the second servo machine box 8 and the fifth pipeline 12, the confining pressure is set by means of the confining pressure sensor 10 after oil filling, and the confining pressure is provided for the soil sample. The axial piston rod 7 on the first servo machine box in the constant-flow seepage system A provides axial pressure for the soil sample. By means of the back pressure, the confining pressure and the axial pressure, complex current crustal stress is simulated, and complex stress cyclic change is simulated. During the test, after back pressure saturation is completed, the water in the first water storage tank 26 enters the base of the cell by means of the first pipeline 16, and permeates and corrodes the soil sample by means of the first open hole, and the porous bottom plate 13 and the water-permeable paper 14 at the lower portion of the soil sample. The soil sample seeps upwards, and the eroded soil particle gushes out by means of the porous bottom plate 13 and the water-permeable paper 14 at the upper end of the soil sample, is conveyed to the bell-mouthed pipeline 28 by means of the fourth pipeline 23 and flows into the multi-stage filter tank 27. The soil particles in the multi-stage filter tank 27 are subjected to graded filtration and collection, and the filtered water flows into the water storage device 30 by means of the sixth pipeline. The turbidimeter 19 on the water storage device is configured to detect whether the soil particles flowing out during seepage erosion are completely filtered. After the test, the multi-stage filter tank 27 is taken down, iron wire meshes with different pore diameters are separated, corresponding soil particles in the iron wire meshes are poured out, dried and weighed, so as to obtain the weight of the eroded soil particles by grading, and basic data are provided for particle component change after the soil sample is eroded.

The test apparatus applies seepage force under a back pressure saturation condition based on a triaxial cell, that is, a triaxial test system and measures a seepage-erosion phenomenon, is suitable for various triaxial instruments, has high compatibility, and may meet different experimental requirements.

What is described above is merely a preferred embodiment of the present invention, the scope of protection of the present invention is not limited to the above embodiment, and all the technical schemes belonging to the idea of the present invention belong to the scope of protection of the present invention. Several improvements and modifications are made by those of ordinary skill in the art without departing from the principles of the present disclosure, which should also be considered as the scope of protection of the present disclosure.

What is claimed is:

1. A triaxial test apparatus for measuring eroded soil particles under action of seepage force, comprising a constant-flow seepage system, a soil particle transport grading measurement system, a large-range volume pressure control vacuum system and a data processing and analyzing system, wherein the constant-flow seepage system is connected to the soil particle transport grading measurement system and the large-range volume pressure control vacuum system by means of pipelines separately, and the constant-flow seepage system, the soil particle transport grading measurement system and the large-range volume pressure control vacuum system are connected to the data processing and analyzing system by means of lines separately; the constant-flow seepage system comprises a triaxial cell, an axial-force applying unit and a confining pressure applying unit, the triaxial cell comprising a cell outer cover, a base and a top cap, wherein a soil sample is arranged between the base and the top cap, the cell outer cover is mounted on the base, a taper hole is provided in the base, a first open hole and a second open hole are provided in the taper hole, the first open hole is connected to the large-range volume pressure control vacuum system by means of a first pipeline, a first flowmeter is arranged on the pipeline, the second open hole is connected to a confining pressure device by means of a second pipeline, the top cap is provided with an inverted taper hole, a third open hole and a fourth open hole are provided in the inverted taper hole, the third open hole is connected to a pressure sensor by means of a third pipeline, the fourth open hole is connected to the soil particle transport grading measurement system by means of a fourth pipeline, and a sensor and a second flowmeter are arranged on the fourth pipeline.

2. The triaxial test apparatus for measuring eroded soil particles under action of seepage force according to claim 1, wherein the soil particle transport grading measurement system comprises a first water storage tank and a multi-stage filter tank, the multi-stage filter tank being arranged in the first water storage tank, a water inlet is provided in the first water storage tank, an end, located in an inner cavity of the first water storage tank, of the water inlet is connected to a bell-mouthed pipeline, the other end of the bell-mouthed pipeline is in butt joint with the multi-stage filter tank, an end, located outside the first water storage tank, of the water inlet is provided with a first volume pressure controller, the first volume pressure controller is connected to the constant-flow seepage system by means of the fourth pipeline, and a water storage device is connected to a bottom of the first water storage tank by means of a sixth pipeline.

3. The triaxial test apparatus for measuring eroded soil particles under action of seepage force according to claim 2, wherein one side of the first water storage tank is connected to a first air pump by means of a seventh pipeline, a two-way valve is arranged at a joint of the first water storage tank and the pipeline, a third flowmeter is arranged on the sixth pipeline, and a turbidimeter is arranged on the water storage device.

4. The triaxial test apparatus for measuring eroded soil particles under action of seepage force according to claim 3, wherein the large-range volume pressure control vacuum system comprises a second water storage tank and a second air pump, a blade fan is mounted in the second water storage tank, a two-way valve is arranged at an opening in one side of the second water storage tank, the second air pump is connected to the two-way valve by means of an eighth pipeline, an external second volume pressure controller is connected to a bottom of the second water storage tank by means of a pipeline, and the second volume pressure controller is connected to the constant-flow seepage system by means of the first pipeline.

5. The triaxial test apparatus for measuring eroded soil particles under action of seepage force according to claim 1, wherein the axial applying unit comprises a first servo machine box and an upper cover, the base is mounted on the first servo machine box, the first servo machine box is connected to an axial piston rod, an upper portion of the axial piston rod is connected to the base, the upper cover is arranged on the top cap, and the upper cover is provided with an axial displacement sensor and an axial pressure sensor; and the confining pressure applying unit comprises a second servo machine box, an oil tank and a confining pressure device, the confining pressure device being connected to the base by means of a pipeline, and the oil tank being mounted on the second servo machine box and connected to the base by means of a fifth pipeline, and the base is in communication with an inner cavity of the cell.

6. The triaxial test apparatus for measuring eroded soil particles under action of seepage force according to claim 5, wherein the data processing and analyzing system comprises a data acquisition device and a computer, the computer being connected to the data acquisition device by means of a line, and the first volume pressure controller, the second volume pressure controller, the first flowmeter, the second flowmeter, the third flowmeter, the confining pressure device, the pressure sensor, the sensor, the axial displacement sensor and the axial pressure sensor are connected to the data acquisition device by means of lines separately.

7. The triaxial test apparatus for measuring eroded soil particles under action of seepage force according to claim 6, wherein an upper end and a lower end of the soil sample are provided with a porous bottom plate and water-permeable paper respectively.

8. The triaxial test apparatus for measuring eroded soil particles under action of seepage force according to claim 7, wherein the multi-stage filter tank consists of at least three steel wire mesh layers, and the steel wire mesh layers have different pore diameters.

9. The triaxial test apparatus for measuring eroded soil particles under action of seepage force according to claim 8, wherein the taper hole and the inverted taper hole are funnel-shaped.

* * * * *